(12) United States Patent
Büttner

(10) Patent No.: US 8,979,085 B2
(45) Date of Patent: Mar. 17, 2015

(54) SAMPLE HOLDER OF A MICROTOME

(71) Applicant: Leica Biosystems Nussloch GmbH, Nussloch (DE)

(72) Inventor: René Büttner, Mannheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

(21) Appl. No.: 14/186,865

(22) Filed: Feb. 21, 2014

(65) Prior Publication Data

US 2014/0246823 A1  Sep. 4, 2014

(30) Foreign Application Priority Data

Mar. 1, 2013 (DE) .................. 10 2013 203 564

(51) Int. Cl.
*G01N 1/06* (2006.01)

(52) U.S. Cl.
CPC .................................. *G01N 1/06* (2013.01)
USPC .............................................. 269/75; 269/95

(58) Field of Classification Search
USPC .......... 269/3, 6, 95, 168–171.5, 197–19, 203, 269/209
See application file for complete search history.

(56) References Cited

U.S. PATENT DOCUMENTS

| | | | | |
|---|---|---|---|---|
| 5,775,679 | A * | 7/1998 | Strub .............................. | 269/75 |
| 6,554,264 | B1 * | 4/2003 | Alford ........................... | 269/147 |
| 7,066,457 | B2 * | 6/2006 | Gerritsen et al. ................. | 269/6 |
| 8,678,363 | B2 * | 3/2014 | Baker ............................. | 269/45 |
| 2009/0026679 | A1 * | 1/2009 | Harman, III .................... | 269/43 |

FOREIGN PATENT DOCUMENTS

| | | |
|---|---|---|
| DE | 2 143 529 | 3/1973 |
| DE | 36 07 766 | 5/1987 |
| DE | 37 14 389 | 6/1988 |
| DE | 37 14 411 | 7/1988 |
| DE | 195 16 468 | 8/1996 |
| DE | 196 04 001 | 8/1997 |
| DE | 199 11 173 | 10/2000 |
| DE | 103 24 696 | 12/2004 |

* cited by examiner

*Primary Examiner* — Lee D Wilson

(74) *Attorney, Agent, or Firm* — Hodgson Russ LLP

(57) ABSTRACT

A sample holder (100) of a microtome is described, including a basic body (110) and an alignment component (120). A first actuatable retainer (140) can be configured to permit a relative motion between the alignment component (120) and the basic body (110) in an actuated state, and configured to inhibit the relative motion between the alignment component (120) and the basic body (110) in a deactuated state. A clamping subassembly (130) can be arranged on the alignment component (120), and comprise two clamping components (131, 132). A second actuatable retainer (180) can be configured to open the clamping subassembly (130) in an actuated state, and configured to close the clamping subassembly (130) in a deactuated state. An actuation mechanism can be configured to respectively actuate and deactuate the first actuatable retainer (140) and the second actuatable retainer (180).

11 Claims, 3 Drawing Sheets

SAMPLE HOLDER OF A MICROTOME

CROSS REFERENCE TO RELATED APPLICATIONS

This application claims priority of German patent application number 10 2013 203 564.0 filed Mar. 1, 2013, the entire disclosure of which is incorporated by reference herein.

FIELD OF THE DISCLOSURE

The present disclosure relates to a sample holder for a microtome.

BACKGROUND OF THE DISCLOSURE

After appropriate preparation, it is possible with a microtome to remove tissue sections that are only a few micrometers thick. The sample to be sectioned must be delivered to the microtome, and must be clamped therein for reliable sectioning. DE 199 11 173 A1 describes a sample holder for a microtome in which a sample received in the sample holder can be aligned in motorized fashion relative to the sectioning plane, and can be preset in motorized fashion onto the blade. The high risk of injury from the blade of the microtome can thereby already be reduced. Handling of the samples and sections, however, is still performed manually: the sample (usually a cassette having tissue embedded in paraffin) must be manually clamped into the sample holder. Because sample changing takes place in the vicinity of the blade of the microtome, an elevated risk of injury continues to exist here.

It is therefore desirable in this context also to automate activities that have hitherto still been carried out manually, in order to further reduce the risk of injury to the user. An initial prerequisite for automated sample changing is creation of a simple, automatable capability for retaining and releasing the sample in the sample holder.

SUMMARY OF THE DISCLOSURE

The present disclosure proposes a sample holder for a microtome described herein. Advantageous embodiments are described throughout the present disclosure.

According to one embodiment, a sample holder of a microtome includes a basic body, an alignment component mounted movably relative to the basic body, a first actuatable retaining means which is embodied so that in the actuated state it permits a relative motion between the alignment component and the basic body, and in the deactuated state it inhibits a relative motion between the alignment component and the basic body, a clamping subassembly, arranged on the alignment component, comprising two clamping components movable relative to one another, a second actuatable retaining means which is embodied so that in the actuated state it opens the clamping subassembly and in the deactuated state it closes the clamping subassembly, an actuation mechanism which is embodied so that upon actuation it actuates firstly the first actuatable retaining means so that it permits a relative motion between the alignment component and the basic body and then the second actuatable retaining means so that it opens the clamping subassembly, and upon deactuation it deactuates firstly the second actuatable retaining means so that it inhibits a relative motion between the alignment component and the basic body, and then the first actuatable retaining means (140) so that it closes the clamping subassembly.

A sample holder according to the present disclosure offers a simple and automatable capability for retaining and releasing a sample in the sample holder. This allows activities that hitherto were still carried out manually to be automated, and thus allows the risk of injury to the user to be further reduced.

The disclosure additionally offers the capability of immobilizing the sample holder, after it has been aligned, using the same mechanism, and thus securing it against changes in alignment resulting in particular from the sectioning operation. This avoids problems that can occur with motorized alignment. For example, the self-locking of the spindles of drive systems is often not sufficient to effect sufficient retention of the alignment.

The sample holder is embodied in such a way that retention of the sample and immobilization of the sample holder are caused by the same actuation mechanism, but take place successively. The actuation mechanism can thus be actuated by a single electrical drive system, which keeps the physical and control-engineering complexity low. The actuation sequence is advantageously adapted to the handling sequence, i.e. firstly the sample is retained in the sample holder, then the capability should exist for aligning it, and only then is the sample holder to be immobilized.

According to a preferred embodiment, a (preferably motor-actuated) passive spring mechanism is used, such that both retention of the sample in the sample holder and immobilization of the sample holder are brought about by spring force. For example, in the event of a power failure an active spring mechanism (in which a drive system tensions a spring) would have the disadvantage that the retention of both components would be discontinued, and both the sample and the microtome might be damaged during the sectioning motion. An elevated risk of injury to the user would also exist.

Further advantages and embodiments of the disclosure are evident from the description and the appended drawings.

It is understood that the features recited above and those yet to be explained below are usable not only in the respective combination indicated, but also in other combinations or in isolation, without departing from the scope of the present disclosure.

BRIEF DESCRIPTION OF THE DRAWINGS

The disclosure is schematically depicted in the drawings on the basis of an exemplifying embodiment, and will be explained in detail below with reference to the drawings, in which.

DETAILED DESCRIPTION OF THE DISCLOSURE

Figure 1:
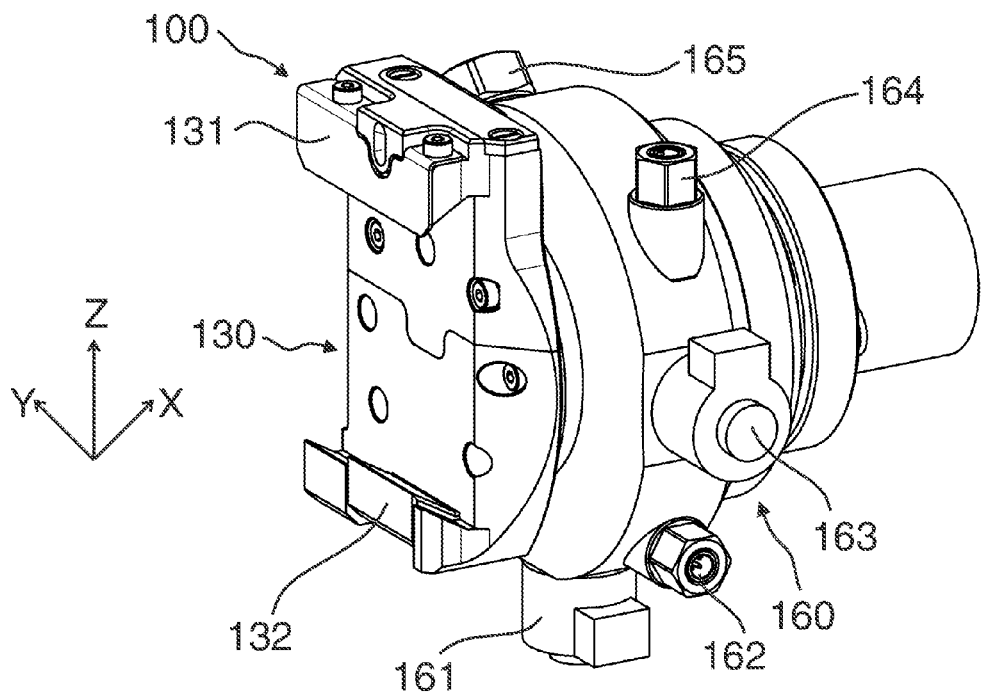
FIG. 1 is a perspective view schematically showing a sample holder obliquely from the front.

The Figures depict a preferred embodiment of a sample holder 100 according to the present disclosure. Sample holder 100 comprises a basic body 110 that constitutes a stationary reference system for the sample holder. Sample holder 100 furthermore comprises an alignment component 120 mounted movably relative to basic body 110, which component here comprises a clamping subassembly fastening element 121, a bearing sleeve element 122, and a counter-bearing element 123. Clamping subassembly fastening element 121 is connected immovably to bearing sleeve element 122. A clamping subassembly 130 is arranged on clamping subassembly fastening element 121. Counter-bearing element 123 is mounted slidably on bearing sleeve element 122. Sample holder 100 comprises an automatic actuation mechanism in order on the one hand to retain alignment component 120 relative to basic body 110, and on the other hand to open and close clamping subassembly 130.

A first actuatable retaining means 140 is provided, which comprises a first spring means embodied here as actuation spring 142 and a first actuatable spacing means embodied here as lever 141. Actuation spring 142 is arranged between counter-bearing element 123 and bearing sleeve element 122, and thereby on the one hand pulls clamping subassembly fastening element 121 of alignment component 120 toward basic body 110 accompanied by formation of a front clamping surface 143, and on the other hand pushes counter-bearing element 123 of alignment component 120 toward basic body 110 accompanied by formation of a rear clamping surface 144. Clamping surfaces 143 and 144 inhibit a relative motion between alignment component 120 and basic body 110.

Figure 3:
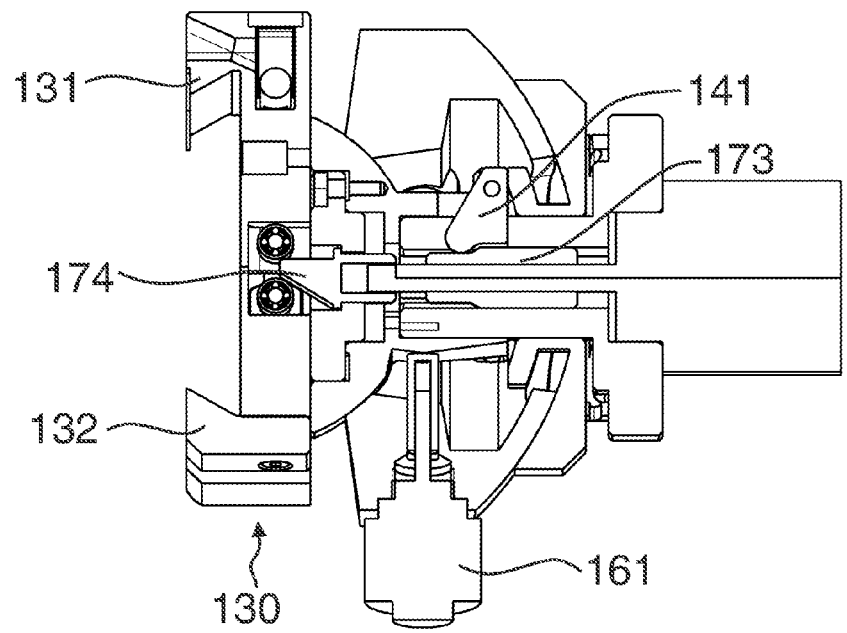
FIG. 3 is a longitudinally sectioned view of the sample holder including the clamping subassembly, the two retaining means being in the deactuated state.
Figure 4:
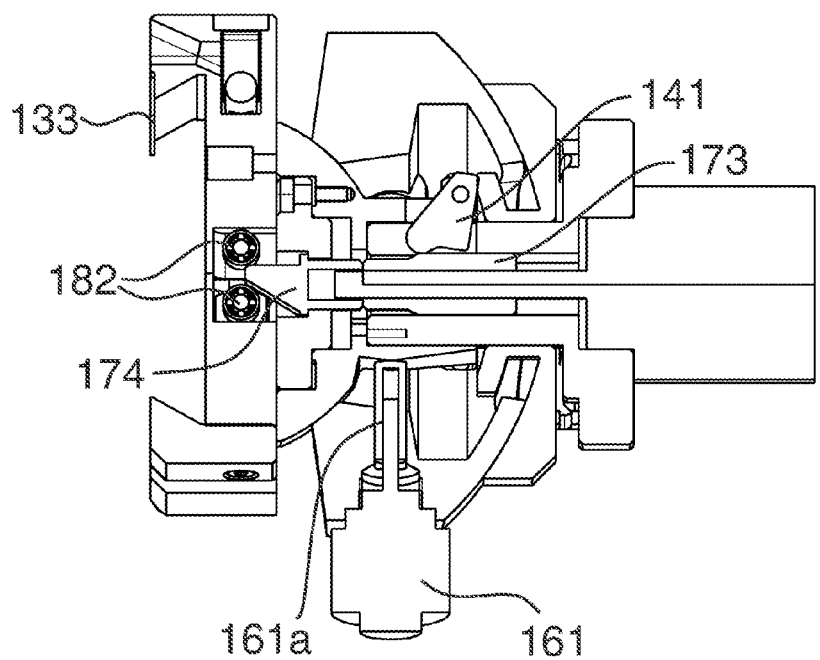
FIG. 4 is a longitudinally sectioned view of the sample holder, the first retaining means being in the actuated state.
Figure 5:
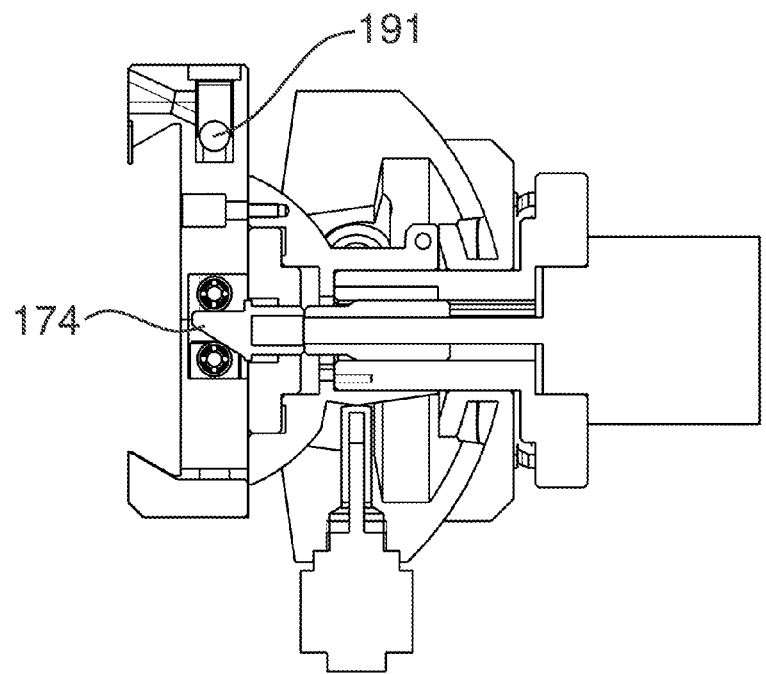
FIG. 5 is a longitudinally sectioned view of the sample holder, both retaining means being in the actuated state.

A drive subassembly 160 that is arranged on or in basic body 110 is provided here in order to align alignment component 120 relative to basic body 110. Drive subassembly 160 comprises two electric motors 161, 163 and two associated position sensors 162, 164. A spring-loaded counter-bearing bolt 165 is also provided. Sleeve-shaped spindle nuts, of which only one spindle nut 161a is illustrated here in FIGS. 3 to 5, are translationally acted upon by electric motors 161, 163. The spindle nuts push against alignment component 120, and the latter pushes against counter-bearing bolt 165, so that a pivoting of alignment component 120 relative to basic body 110 around a Y axis (electric motor 161) and a Z axis (electric motor 163) is possible. A "zero position" refers respectively to the alignment in which a front surface 121b of alignment component 120 is aligned parallel to a sectioning plane via a blade of a microtome.

Alignment component 120 comprises, on clamping subassembly fastening element 121, a swivel head 121a that coacts with an associated swivel socket 110a of basic body 110 so that a pivoting of alignment component 120 relative to basic body 110 becomes possible, and clamping surface 143 can nevertheless be constituted in any pivot position. In the present embodiment, basic body 110 likewise comprises a swivel head 110b that coacts with an associated swivel socket 123b of counter-bearing element 123, so that a pivoting of alignment component 120 relative to basic body 110 becomes possible, and clamping surface 144 can nevertheless be constituted in any pivot position.

Once the clamping is released, the alignment of alignment component 120 (and thus of clamping subassembly 130 and thus of a sample held in the clamping subassembly) can be accomplished by actuating electric motors 161, 163. The spindle nuts thereof respectively push against a defined surface of alignment component 120 so that the latter pivots correspondingly around a rotation point that is constituted by a preferably common spherical center point of swivel sockets 110a, 123b. Counter-bearing bolt 165 provides the counter-force needed in order to hold the position. Position sensors 162, 164 are embodied here as inductive sensors and detect the presence of the spindle nuts, and can thus determine the alignment zero position. It is proposed to tilt position sensors 162, 164 toward the respective electric motor 161, 163 so that the outward and inward motion of the spindle nuts can be sensed. Sensors having a sufficient range and a suitable arrangement can detect the spindle nuts over the entire stroke length. From the distance thereby measurable, an accurate determination of the angular position around the corresponding axis is possible.

An electrical spindle drive system 170 comprising an electric motor 171, a threaded spindle 172 driven by electric motor 171, and a spindle nut 173 sitting on threaded spindle 172 is arranged on bearing sleeve element 122. A rotational motion of electric motor 171 and thus of threaded spindle 172 can thereby be converted into a translational motion of spindle nut 173. The use of a compact spindle motor eliminates complex and bulky gear systems.

Figure 2:
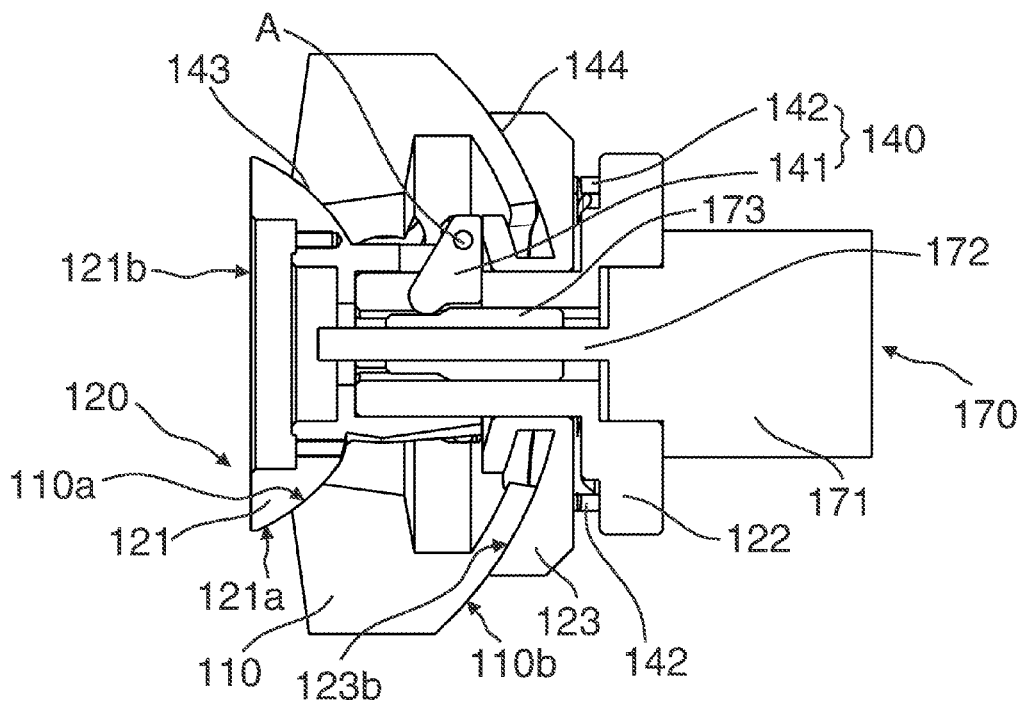
FIG. 2 is a longitudinally sectioned view of the sample holder without the clamping subassembly.

When spindle nut 173 is moved to the left starting from the deactuated position depicted in FIGS. 2 and 3, firstly the first actuatable retaining means 140 is actuated (FIG. 4). More precisely, in this case lever 141 is actuated by being pivoted around a rotation axis A that is stationary relative to clamping subassembly fastening element 121. As a result, counter-bearing element 123 is pushed against the spring force away from clamping subassembly fastening element 121, so that both clamping surfaces 143 and 144 are unloaded. Preferably, several such levers are provided around the periphery in order to push counter-bearing element 123 uniformly away from clamping subassembly fastening element 121.

Figure 6:
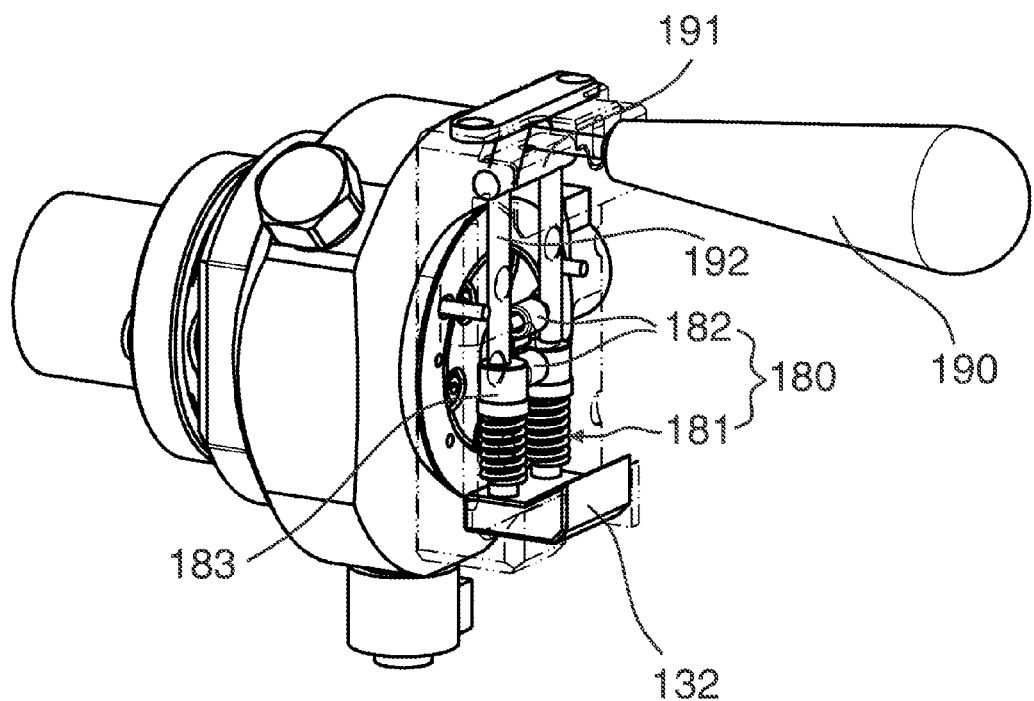
FIG. 6 is a perspective view of the sample holder obliquely from the front, the clamping subassembly being depicted as partly transparent in order to depict the emergency actuation mechanism.

As explained, clamping subassembly 130 is arranged on clamping subassembly fastening element 121. Clamping subassembly 130 possesses two clamping components 131, 132 movable relative to one another; here, upper clamping component 131 is immovable and lower clamping component 132 is movable. As is evident in FIG. 6, lower clamping component 132 is braced against upper clamping component 131 by means of compression springs 181 constituting a second spring means. This neutral position represents the closed state of clamping subassembly 130. It is advantageously possible to provide a securing panel 133 that, in the opened state, ensures that the sample does not tip forward.

A second actuatable retaining means 180, which is embodied so that in the actuated state it opens clamping subassembly 130 and in the deactuated state it closes clamping subassembly 130, is provided in order to open and close clamping subassembly 130. Second actuatable retaining means 180 comprises compression springs 181 as well as a second actuatable spacing means 182 that here comprises a recess having two needle bearings.

Also provided is a second actuation element, embodied here as a wedge 174, for actuation of second actuatable retaining means 180. Wedge 174 can engage into the recess and thus actuate second actuatable spacing means 182. The needles, and thus clamping component 131, 132 that are immovably connected to the needle bearings, are pushed apart.

When spindle nut 173 is moved farther to the left, starting from the position depicted in FIG. 4 in which first actuatable retaining means 140 is actuated, second actuatable retaining means 180 is also actuated (FIG. 5). More precisely, in this case second actuatable spacing means 182 is actuated, by the fact that wedge 174 is pushed between the needle bearings by spindle nut 173.

As a result of its angle, the wedge converts the axial force via the lower needle bearing into a downward force acting radially with respect to the axis of threaded spindle 172. The upper needle bearing is rigid, and accepts the radial counter-force in order to unload threaded spindle 172. Because only the friction between levers 141 and spindle nut 172 must be overcome in order to release the alignment clamping, almost all of the motor force is available for opening the clamping subassembly. The wedge drives the lower bearing downward. The latter is connected via two spring-loaded bolts 183 to the movable lower clamping component 132. The result is that the two clamping components 131, 132 are pushed apart, and clamping subassembly 130 is opened. A sample can then be inserted or taken out.

Upon backward travel of spindle nut 173, lower clamping component 132 is moved back again by compression springs 181 guided by the bolts, and clamping subassembly 130 is closed. Wedge 174 is likewise moved axially back, as a result of its angle and via the bearing, in the absence of the self-locking. When spindle nut 173 is moved back further, levers 141 are again moved back, by actuation spring 142 via counter-bearing element 123, along the bevels on spindle nut 173, until they are in their initial position. As a result of the geometric properties, the alignment is retained once the clamping subassembly has been closed. In reverse, firstly the alignment is released and then the clamping subassembly is opened. Secure retention of the sample in clamping subassembly 130 is thus ensured, while alignment of the sample surface can be performed by the user.

For manual removal of the sample (for example in the case of a power failure), a manually actuatable emergency actuation mechanism is present which is embodied so that upon actuation, it actuates only second actuatable retaining means 180. As is evident from FIG. 6, for this a separate lever 190 can be introduced into the upper part of clamping subassembly 130. The upward motion of lever 190 causes the resulting torque to be converted by a transverse bolt 191 into an axial force downward. In that context, two symmetrically arranged cylindrical pins 192 push onto bolts 183 that are connected to lower clamping component 132. The motion of lever 190 causes clamping subassembly 130 to be opened in a manner decoupled from the automatic actuation mechanism, so that a sample can be removed from clamping subassembly 130.

The disclosure is not to be limited to the specific embodiments disclosed, and modifications and other embodiments are intended to be included within the scope of the disclosure.

What is claimed is:

1. A sample holder (100) of a microtome, comprising
a basic body (110);
an alignment component (120) mounted movably relative to the basic body (110);
a first actuatable retaining means (140) configured to permit a relative motion between the alignment component (120) and the basic body (110) in an actuated state, and configured to inhibit the relative motion between the alignment component (120) and the basic body (110) in a deactuated state;
a clamping subassembly (130) arranged on the alignment component (120), comprising two clamping components (131, 132) movable relative to one another;
a second actuatable retaining means (180) configured to open the clamping subassembly (130) in an actuated state, and configured to close the clamping subassembly (130) in a deactuated state;
an actuation mechanism configured such that:
upon actuation, the actuation mechanism is configured to first actuate the first actuatable retaining means (140) such that the relative motion between the alignment component (120) and the basic body (110) is permitted, and then configured to actuate the second actuatable retaining means (180) such that the clamping subassembly (130) is opened; and
upon deactuation, the actuation mechanism is configured to first deactuate the second actuatable retaining means (180) such that the clamping subassembly (130) is closed, and then configured to deactuate the first actuatable retaining means (140) such that the relative motion between the alignment component (120) and the basic body (110) is inhibited; and
an electrical drive system (170) configured to drive the actuation mechanism.

2. The sample holder according to claim 1, wherein the actuation mechanism includes a first actuation element (173) configured to actuate the first actuatable retaining means (140), the first actuation element (173) being configured to move translationally upon actuation of the actuation mechanism.

3. The sample holder according to claim 2, wherein the actuation mechanism includes a spindle drive system (170) configured to translationally move the first actuation element.

4. The sample holder according to claim 1, wherein the actuation mechanism includes a second actuation element (174) configured to actuate the second actuatable retaining means (180), the second actuation element (174) being configured to move translationally upon actuation of the actuation mechanism.

5. The sample holder according to claim 4, wherein the actuation mechanism includes a spindle drive system (170) configured to translationally move the second actuation element.

6. The sample holder according to claim 1, wherein the first actuatable retaining means (140) includes a first spring means (142) configured to urge the alignment component (120) toward the basic body (110), and a first actuatable spacing means (141) that in an actuated state, is configured to lift the alignment component (120) away from the basic body (110).

7. The sample holder according to claim 1, wherein the second actuatable retaining means (180) includes a second spring means (181) configured to urge the two clamping components (131, 132) toward one another, and a second actuatable spacing means (182) that in an actuated state, is configured to push the two clamping components (131, 132) away from one another.

8. The sample holder according to claim 1, wherein a first element selected from the following includes a swivel socket: the basic body (110) and alignment component (120), and a second element, different from the first element, selected from the following includes a swivel head: the basic body (110) and alignment component (120).

9. The sample holder according to claim 1, further comprising an electrical drive subassembly (160) configured to align the alignment component (120) relative to the basic body (110).

10. The sample holder according to claim 9, wherein the electrical drive subassembly (160) includes two electrical drive systems (161, 163) arranged such that the alignment component (120) is pivotable about two different rotation axes relative to the basic body (110).

11. The sample holder according to claim 1, further comprising a manually actuatable emergency actuation mechanism configured such that, upon actuation, only the second actuatable retaining means (180) is actuated.

* * * * *